United States Patent [19]

Stalberg

[11] Patent Number: 4,594,159

[45] Date of Patent: Jun. 10, 1986

[54] PROCESS AND APPARATUS FOR APPLYING BACK PRESSURE IN A LIQUID CHROMATOGRAPHY SYSTEM

[75] Inventor: Ralph I. Stalberg, Upsala, Sweden

[73] Assignee: Pharmacia AB, Upsala, Sweden

[21] Appl. No.: 667,155

[22] Filed: Nov. 1, 1984

[30] Foreign Application Priority Data

Nov. 17, 1983 [SE] Sweden .................. 8306332

[51] Int. Cl.$^4$ .............................. B01B 15/08
[52] U.S. Cl. .................. 210/198.2; 210/656
[58] Field of Search ........... 210/656, 659, 130, 139, 210/198.2

[56] References Cited

U.S. PATENT DOCUMENTS

| | | | |
|---|---|---|---|
| 2,536,663 | 1/1951 | Schaer | 210/130 |
| 3,783,590 | 1/1974 | Allen | 210/133 |
| 3,984,314 | 10/1976 | Ernst et al. | 210/198.2 |
| 4,137,161 | 1/1979 | Shimada et al. | 210/659 |

FOREIGN PATENT DOCUMENTS 1399397  7/1975  United Kingdom .

OTHER PUBLICATIONS

Patent Abstracts of Japan, abstract of JP 52-15394, pub. 4/2/77.
Derwent's Abstract No. 21 556 E/11, SE 832 473.

*Primary Examiner*—John Adee
*Attorney, Agent, or Firm*—Fred Philpitt

[57] ABSTRACT

The present invention is concerned with a process and apparatus for generating back pressure in a liquid chromatography system, in that the eluent after having passed through the detector cell is caused to pass through a valve, said valve generating a back pressure and having for this purpose a passage (A-B) which is formed, at an interface between two bodies (20, 24), only when a sufficiently high liquid pressure has been attained, at least one of said bodies being a body of an elastic material.

4 Claims, 3 Drawing Figures

PROCESS AND APPARATUS FOR APPLYING BACK PRESSURE IN A LIQUID CHROMATOGRAPHY SYSTEM

The present invention is concerned with a process for applying back pressure in a liquid chromatography system so as to prevent the formation of air bubbles, and with an apparatus for generating such back pressure.

The main constituent parts of a liquid chromatography separation system are a pump, a sample injector, a separation column, a detector and, optionally, a fraction collector. In the separation column, the sample that has been applied is separated into its individual components or groups of components in accordance with any one of the chromatographical separation techniques such as e.g. gel filtration, ion exchange chromatography or affinity chromatography. The liquid effluent from the column then passes further on to a detector. A characteristic property of the effluent such as e.g. absorbance, fluorescence, conductivity or electrochemical potential is measured by means of the detector and serves as a basis for a qualitative and/or quantitative analysis of the sample. In certain cases isolation of some particular component(s) of the sample is desired; this may be effected by means of a so-called fraction collector which collects the liquid portion containing said component(s), after recording thereof in the detector.

In many types of practical applications, separation in the column is brought about in the following manner: When the sample has been injected into the column and certain components thereof have become bound to stationary groups in the separation medium the sample is exposed to an altered environment causing a change in binding properties, so that then elution of the separated components will be feasible. The said alteration or change of the environment is achieved by altering the composition of the eluant, for example by mixing two or more liquids in varying relative proportions.

In so-called RPC (Reversed Phase Chromatography) the polar properties of the eluant are altered by means of e.g. mixing an aqueous solution and an organic liquid such as acetonitrile, isopropanol or methanol. Mixing of the liquids is effected by pumping them in suitable proportions into a mixing chamber designed so as to produce a homogeneous eluant.

For the separation to be efficient it is important that the separation medium in the column should have a large surface area for contact with the sample solution; in order to ensure such a large surface area the separation medium is usually employed in the form of small spherical particles. HPLC techniques (techniques employing High Performance Liquid Chromatography) such as they have now been developed, involving pumping of the eluant through the column at a high rate of flow, require an increased contact area in order for the same degree of separation to be maintained. This increase of the area means that the particle size has to be reduced; and this in turn calls for higher pressures for forcing the eluant through the column. Since, however, flow resistance after the column is normally low there will then occur a considerable pressure drop which will promote the generation of air bubbles in all those cases where the liquid contains dissolved air. Especially in RPC separation procedures air bubbles have been found to constitute a major problem. The bubbles which will form directly after the column or in the detector cell are apt to adversely affect the output signal and often to severely blur the result obtained.

Various techniques have been described aimed at reducing these problems; they involve creating a certain amount of back pressure above the detector cell to thus decrease the risk of air bubble formation. The actual amount of back pressure required in each case will vary, depending in the first place on the composition and temperature of the eluant. In the case of RPC procedures, a back pressure of the order of 2 bars is often sufficient. According to one such method a long tube having a small interior diameter is connected to the system at a point after the detector cell. I view of the necessary length of the tube the volume therein is a comparatively large one; this arrangement is therefore unsuitable in cases where it is desired to collect individual fractions, inasmuch as the high resolution of separated components as attained in the column is partly lost again if the so-called dead volume is too great. Moreover the back pressure obtained in this manner is highly flow-sensitive. Another method has been presented according to which the effluent from the column will act on a spring-biassed piston permitting the passage of liquid when the liquid pressure counterbalances the force exerted by the spring. It appears however that in this arrangement, too, the dead volume will be so great as to virtually preclude collection of fractions. In addition there will be resistance problems arising when the system is employed in corrosive environments, e.g. high salt concentrations. According to a third method, a gas such as e.g. helium is bubbled through all the liquids both before and during the separation procedure to thus remove air by entrainment from the liquids. This method does not require any back pressure equipment to be installed after the detector, but it will be appreciated that from an economic point of view this method is not very attractive.

The present invention provides a process for generating a back pressure after the detector cell in a liquid chromatography system, wherein the eluant after having passed through the detector cell is passed into a clearance which is formed, at an interface between two bodies, only when the liquid pressure has become sufficiently high, whereby at least one of said bodies being made of an elastic material. The invention comprises also an apparatus in the form of a valve means for generating the said back pressure. This valve consists of a first body containing a channel which communicates with the detector cell and which has its outlet situated on the body surface and shut off by an elastic second body, a passage through this valve being formed at the first body - second body interface only after the liquid pressure has become sufficiently high. In order for the liquid to flow in a desired direction in the passage between the two bodies the contact pressure of the elastic body is progressively reduced in that direction.

Figure 1:
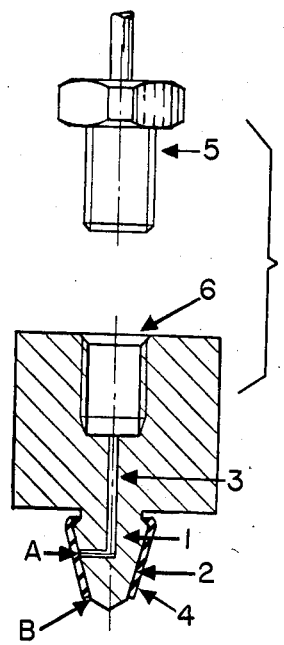
FIGS. 1-3 illustrate the embodiments of the invention.
Figure 2:
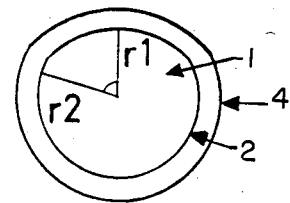

According to one embodiment (FIG. 1), the unit may comprise a nipple having a substantially conical portion (1) and formed with a channel (3) having its outlet opening (A) positioned at a point in the perimeter surface (2) of the conical portion (1). The perimeter surface is coated with an elastic tubular body (4) tightly sealing off the channel outlet (A). Eluent is passed from the detector cell through a tube or similar connecting means attached to the nipple e.g. with the aid of a holder member (5) which is screwed into a threaded recess (6) of the nipple. When the liquid pressure in the channel becomes sufficiently high a passage (A-B) is formed at the interface between the elastic body (4) and the conical nipple surface, leading in a direction towards the conically tapering portion of the nipple. Because of this conically tapering configuration the contact pressure of the elastic body against the nipple will be higher in the direction towards the base of the cone and lower in the direction of taper, the liquid thus being caused to flow in that latter direction. The dead volume will be small, inasmuch as only a short passage is required in the back pressure unit. It is even possible to still further reduce the dead volume by means of limiting the spreading of the liquid on the perimeter surface to substantially a narrow passage A-B, this being achieved by making the radius ($r_1$) to a point on the line A-B slightly shorter than a radius ($r_2$) forming an angle of e.g. 45° or more with the first-named radius ($r_1$) as illustrated in FIG. 2 which is a cross section through the nipple of FIG. 1 perpendicular to the axis of the conical nipple and intersecting the perimeter surface at a point on the line A-B. The contact pressure of the elastic body against the nipple will therefore be somewhat lower in a region close to the line A-B.

The eluent leaves the unit at (B) by falling, in the form of droplets, into a sample container or other collecting vessel. This embodiment of the apparatus is thus suitable for forming the terminal portion of the liquid-delivering part of the arm or similar structure that is commonly placed above the sample containers in a fraction-collecting unit.

Figure 3:
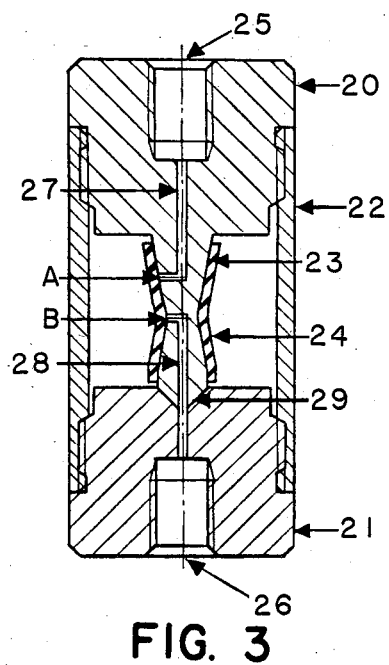

In an alternative embodiment (FIG. 3), the back pressure valve comprises two endpieces (20) and (21) screwed into a threaded tubular member (22), one of said endpieces being formed with a conically tapering portion (23) which is coated with the elastic body (24). Tubes are attached at (25) and (26) with connectors suitable for this purpose. Liquid from the detector cell enters the unit at (25) and passes through the first endpiece, viz. through channel (27) down to (A). Between the conical portion of endpiece (20) and the elastic body (24) a passage (A-B) will be formed only when a sufficient pressure has established itself. At (B) the liquid passes into a channel (28) in the endpiece (20) in order to then via tightly sealing connection means (29) pass through the other endpiece (21) and thence out of the unit at (26). In order to ensure (i) that the liquid upon having reached level (B) will pass into the channel (28) and (ii) that the elastic body will retain its correct position the endpiece (20) has been given a diameter increasing in both directions from the inlet opening (B) of channel (28).

In these two examples, the passage has been formed at the interface between a body having a conically tapering portion and a tubular elastic body; but of course it is possible to obtain the same effect by means of other embodiments utilizing the inventive concept.

In the practical use of the invention, different back pressures will be required for various applications and it is therefore desirable to have an optional back pressure. Alteration of the back pressure parameter can be achieved in a simple manner, for example in that the contact pressure of the elastic body is altered, e.g. by choosing a material of a different elasticity. In cases where the elastic body is a tube the interior diameter and thickness of the tube wall may be varied to thus give the desired back pressure properties.

The back pressure generated in accordance with the present invention is substantially independent of the liquid flow rate, within a wide range of flow rates. Experiments have shown that the apparatus according to the two above-illustrated embodiments will produce a less than 10% alteration in back pressure when the flow rate is changed from near zero to 16 ml/min. Furthermore the dead volume is very small, and this method is therefore particularly suitable whenever it is desired to collect sample components in fractions. In view of the rich choice of construction materials available, a high degree of resistance to solvents may be obtained where this is required. The conical portion of the body may suitably be made of e.g. polypropylene or Tefzel ® (Du Pont) for good resistance to solvents. The elastic body may be for instance a silicone tube or, if solvent resistance requirements are high, it may be made of a perfluoro elastomer such as e.g. Kalrez ® (Du Pont).

I claim:
1. In a liquid chromatography system that includes an outlet passageway for the removal of liquid from said system, the improvement consisting of
    (a) an outlet passageway that is discontinuous to the extent that it has a first section that has a first outlet and a second section that has an inlet and a second outlet, and
    (b) an elastic envelope that always extends over and presses toward both said first outlet and the inlet to said second section, said elastic envelope being sufficiently elastic so that when the pressure of the liquid against the interior of said envelope reaches a predetermined value the elastic envelope will be forced outwardly from said first outlet and form a channel along the inner surface of the elastic envelope to said inlet of said second section so as to permit the flow of liquid between said first outlet and the inlet of said second section.
2. The improvement according to claim 1 wherein both said first outlet and the inlet of said second section are located in a member having a changing diameter, said first outlet exiting at a point in the member which has a greater diameter than the point where the inlet of said second section is located, whereby the contact pressure of the elastic envelope against said member decreases progressively from said first outlet to the inlet of said second section.
3. In a liquid chromatography system that includes an outlet passageway for the removal of liquid from said system, the improvement consisting of means for generating back pressure in said passageway, said means including an elastic envelope that always extends over said outlet passageway and presses toward said outlet passageway, but which is sufficiently elastic so that when the pressure of the liquid in said passageway reaches a predetermined value the elastic envelope will be forced outwardly away from said outlet and form a channel along the inner surface of said elastic envelope for the flow of liquid from said outlet passageway.
4. The improvement according to claim 3 wherein said outlet passageway is located in a conically tapering member and said elastic envelope surrounds and presses against said conically shaped member, said formed channel extending from one portion of the exterior of said conically shaped member to a portion of the conically shaped member having a smaller diameter.

* * * * *